United States Patent
Skowerski

(10) Patent No.: US 9,403,738 B2
(45) Date of Patent: Aug. 2, 2016

(54) METATHESIS REACTIONS

(71) Applicant: Apeiron Catalysts Sp. zo.o., Wroclaw (PL)

(72) Inventor: Krzysztof Skowerski, Jablonowo Pomorskie (PL)

(73) Assignee: APEIRON CATALYSTS SP. ZO.O, Wroclaw (PL)

( * ) Notice: Subject to any disclaimer, the term of this patent is extended or adjusted under 35 U.S.C. 154(b) by 251 days.

(21) Appl. No.: 14/219,409

(22) Filed: Mar. 19, 2014

(65) Prior Publication Data

US 2014/0288342 A1 Sep. 25, 2014

Related U.S. Application Data

(60) Provisional application No. 61/803,393, filed on Mar. 19, 2013.

(51) Int. Cl.
| | |
|---|---|
| *B01J 8/00* | (2006.01) |
| *B01J 8/02* | (2006.01) |
| *B01J 19/00* | (2006.01) |
| *B01J 19/24* | (2006.01) |
| *C07C 6/00* | (2006.01) |
| *C07C 6/02* | (2006.01) |
| *C07C 6/04* | (2006.01) |
| *C07C 6/06* | (2006.01) |
| *C07C 67/333* | (2006.01) |
| *C07C 67/475* | (2006.01) |
| *C07D 207/20* | (2006.01) |
| *C07D 313/00* | (2006.01) |
| *C07C 67/00* | (2006.01) |
| *C07C 67/30* | (2006.01) |
| *C07D 207/00* | (2006.01) |
| *C07D 207/02* | (2006.01) |
| *C07D 207/18* | (2006.01) |

(52) U.S. Cl.
CPC . *C07C 6/06* (2013.01); *B01J 8/009* (2013.01); *B01J 8/0221* (2013.01); *B01J 19/2415* (2013.01); *B01J 19/2475* (2013.01); *C07C 67/333* (2013.01); *C07C 67/475* (2013.01); *C07D 207/20* (2013.01); *C07D 313/00* (2013.01); *B01J 2208/00442* (2013.01); *B01J 2208/00539* (2013.01); *B01J 2219/00141* (2013.01); *B01J 2219/00162* (2013.01)

(58) Field of Classification Search
CPC ............... B01J 8/00; B01J 8/009; B01J 8/02; B01J 8/0207; B01J 8/0211; B01J 19/00; B01J 19/24; B01J 19/2415; B01J 19/2475; B01J 2008/00; B01J 2008/00008; B01J 2008/00017; B01J 2008/00433; B01J 2008/00442; B01J 2008/00539; B01J 2219/00049; B01J 2219/00051; B01J 2219/00139; B01J 2219/00141; B01J 2219/0016; C07C 6/00–6/06; C07C 67/00; C07C 67/30; C07C 67/333; C07C 67/475; C07D 207/00; C07D 207/02; C07D 207/18; C07D 207/20; C07D 313/00
See application file for complete search history.

(56) References Cited

U.S. PATENT DOCUMENTS

| | | | | | |
|---|---|---|---|---|---|
| 6,457,209 | B1* | 10/2002 | Breuer | ............... | D01H 13/32 19/150 |
| 2005/0154309 | A1* | 7/2005 | Etchells | ............ | A61B 17/2251 600/459 |
| 2008/0250700 | A1* | 10/2008 | Tremblay | ............... | B01D 61/14 44/301 |

*Primary Examiner* — Natasha Young
(74) *Attorney, Agent, or Firm* — K&L Gates LLP; Brent A. Johnson; Louis C. Cullman

(57) ABSTRACT

Described herein an apparatus and methods used to remove unwanted by-products of metathesis reactions.

24 Claims, 4 Drawing Sheets

METATHESIS REACTIONS

FIELD

The present invention relates to metathesis reactions and apparatus to perform these reactions.

SUMMARY

Described herein are reactors for olefin metathesis reactions. The reactors can be tube-in-tube style reactors that can function in a continuous flow mode. The reactors can comprise an impermeable outer tube and an inner semi-permeable tube wherein a reaction zone is defined between an inner surface of the impermeable outer tube and an outer surface of the inner semi-permeable tube, and wherein contents of the inner semi-permeable tube are pumped away using a vacuum source. In one embodiment, one or more by-products can travel between the reaction zone and the inner semi-permeable tube.

Also described are reactors for olefin metathesis reactions comprising: an impermeable outer tube and an inner semi-permeable tube, wherein the reaction zone is defined within the semi-permeable tube, and wherein the contents of the space defined between inner surface of the impermeable outer tube and an outer surface of the inner semi-permeable tube are pumped away using a vacuum source. Substrates and optionally catalysts can be directed at one end of a reactor and products can be extracted from the other end of the reactor. In some embodiments, a heterogeneous catalyst can be used.

Methods of performing olefin metathesis reactions in a continuous flow mode are also described comprising: reacting at least one substrate and at least one catalyst in a reaction zone of a tube-in-tube reactor, wherein the tube-in-tube reactor includes an impermeable outer tube and an inner semi-permeable tube. In some embodiments, the reaction zone is defined between an inner surface of the impermeable outer tube and an outer surface of the inner semi-permeable tube, and wherein the contents of the inner semi-permeable tube are pumped away using a vacuum source. In other embodiments, the reaction zone is defined within the semi-permeable tube, and wherein the contents of the space defined between the inner surface of the impermeable outer tube and the outer surface of the inner semi-permeable tube are pumped away using a vacuum source.

DETAILED DESCRIPTION

Described herein are apparatus and methods used to remove unwanted by-products of metathesis reactions. Removal of unwanted byproducts, e.g., ethylene, evolved or produced during metathesis reactions can have positive effects on catalyst efficiency. Generally, the apparatus include a tube-in-tube reactor including an inner semi-permeable tube.

Described herein are processes of carrying out olefin metathesis reactions in a continuous flow mode in a tube-in-tube reactor. The processes can allow for efficient removal of unwanted by-products such as, but not limited to, ethylene.

Substrates for olefin metathesis reactions can include, but are not limited to acyclic dienes, terminal and internal alkenes, alkynes, or compounds including these groups.

Catalysts for olefin metathesis reactions can include, but are not limited to ruthenium catalysts, such as Grubbs type catalysts, Hoveyda-Grubbs type catalysts, and Indenylidene type catalysts including:

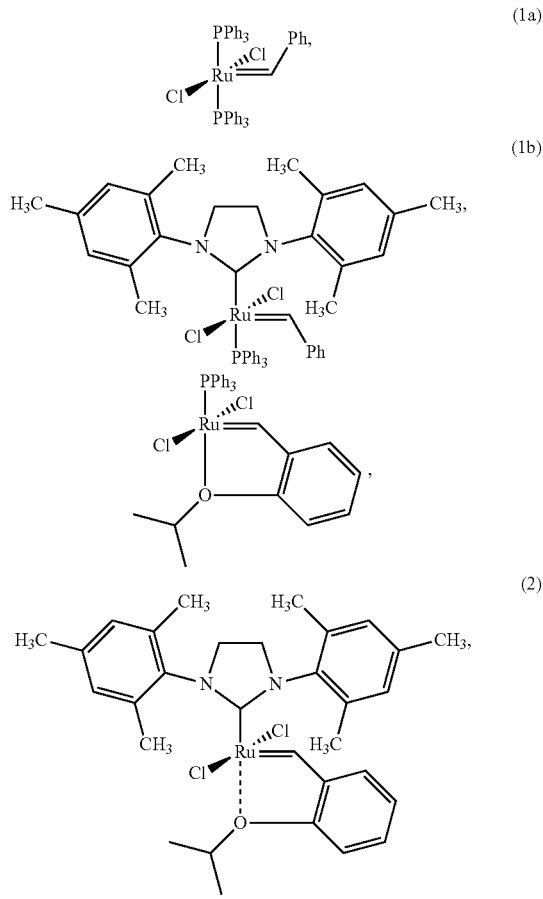

-continued

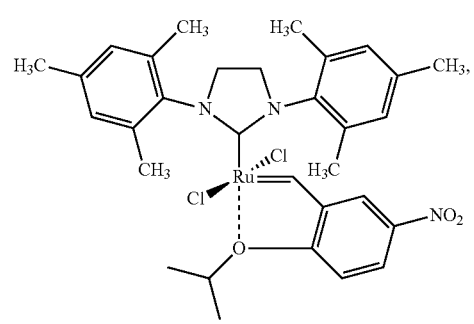
(2')

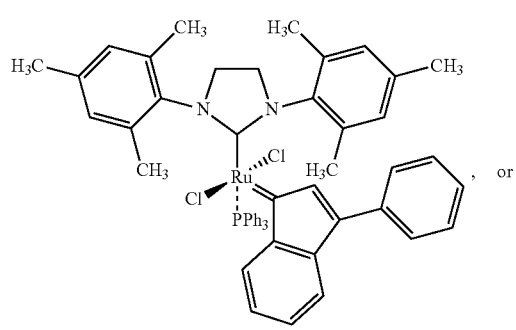
(3)

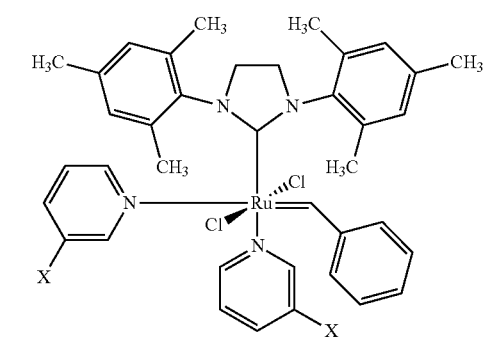

wherein X is H or Br, and, molybdenum catalysts and tungsten catalysts. Heterogenous catalysts can include, but are not limited to

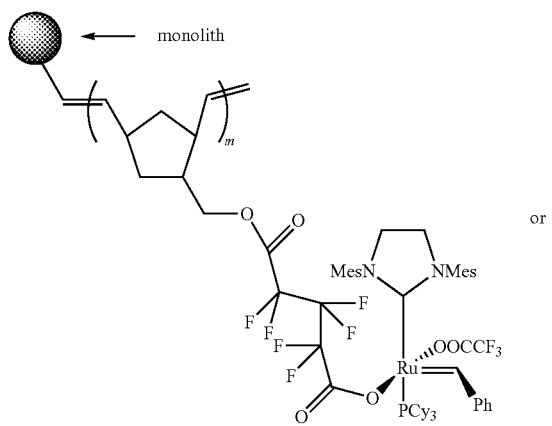

or

-continued

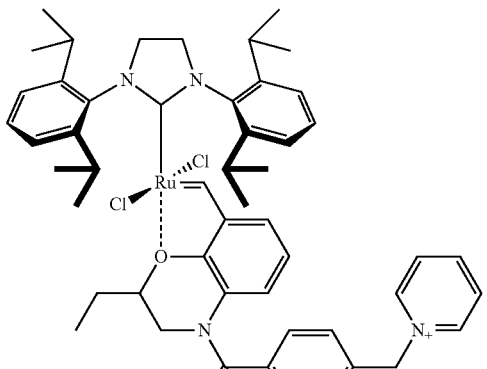
(5)

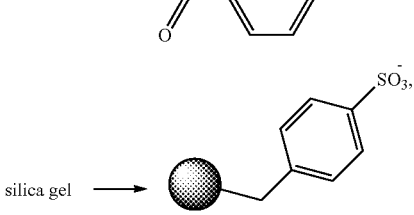

wherein Mes is 2,4,6-trimethylphenyl.

Products of olefin metathesis reactions can include, but are not limited to (macro)cyclic alkenes, internal-acyclic alkenes, polymeric products of acyclic diene metathesis polymerization (ADMET).

By-products of olefin metathesis reactions can include, but are not limited to, ethylene, acetylene, and propylene.

In some embodiments, the tube-in-tube reactors described can have gas flowing in an opposite direction than in processes described in the literature.

Figure 1A:
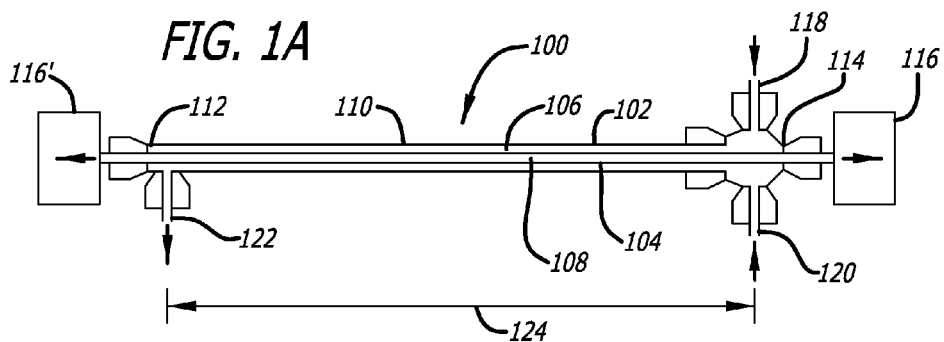
FIG. 1A illustrates an example tube-in-tub reactor configuration.
Figure 1B:
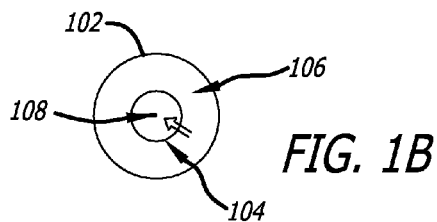
FIG. 1B illustrates a cross section of the tube-in-tub reactor of FIG. 1A.

One example tube-in-tube reactor is illustrated in FIGS. 1A and 1B. Tube-in-tube reactor 100 can include an outer impermeable tube 102 and an inner tube 104 made from a semi-permeable material. Outer impermeable tube 102 and an inner tube 104 are configured to create a first reaction chamber 106 and a second reaction chamber 108. Also, tube-in-tube reactor 100 can include an elongated body portion 110 having a proximal end 112 and a distal end 114. The difference in pressure on both sides of semi-permeable tube, i.e., between first reaction chamber 106 and second reaction chamber 108, can aid in establishing an efficient removal of ethylene from a reaction mixture. Such a pressure differential can be generated by one or more vacuum pumps 116 connected to inner tube 104.

Outer impermeable tube 102 can be formed of any material that prevents substrates, catalyst or products from passing through. In some embodiments, outer impermeable tube 102 can be formed of a polymer such as polyethylene or polypropylene or a metal such as aluminium or stainless steel. If metal, the inner surface of outer impermeable tube 102 can be coated with a non-reactive polymer.

Semi-permeable materials used for inner tube 104 can be any material that allows unwanted by-products to pass through while blocking substantially all other materials of interest. Semi-permeable materials can be permeable to by-products such as alkenes or alkynes having 2 or 3 carbon atoms, but be impermeable to desired hydrocarbons having more than 6 carbon atoms. In other embodiments, semi-permeable materials can be permeable to by-products having 2, 3, 4, or 5 carbon atoms. In still other embodiments, desired hydrocarbons can have more than 5, 6, or 7 carbon atoms.

In other embodiments, permeability can be based on boiling point. For example, a semi-permeable materials can be permeable to by-products having boiling points below about 60° C., below about 40° C., below about 20° C., below about 0° C., below about −20° C., below about −40° C., below about −60° C., or below about −80° C. In still other embodiments, desired hydrocarbons can have a boiling point above about −60° C., above about −40° C., above about −20° C., above about 0° C., above about 20° C., above about 40° C., or above about 60° C.

In one embodiment, a semi-permeable material can allow ethylene, acetylene, and/or propylene to pass through while being resistant to organic solvent passage. In one embodiment, the semi-permeable material can be a polytetrafluoroethylene such as Teflon AF2400™ because it is permeable for ethylene and at the same time is resistant to organic solvents and does not swell.

A metathesis reaction can occur in first reaction chamber 106. In such a case inner tube 104 is connected to vacuum pump 116. This setup may be preferred because it allows for easy and efficient control of reaction temperature by means of traditional heating along elongated body portion 110.

As further illustrated in FIGS. 1A and 1B, distal end 114 of first reaction chamber 106 can include at least two inlet ports. In some embodiments, distal end 114 can include one, two, three, four, five, six, seven, eight, nine, ten, eleven, twelve, thirteen, fourteen, or fifteen inlet ports. In one embodiment, distal end 114 can include a first inlet 118 configured to introduce a catalyst and a second inlet 120 configured to introduce a substrate. Elongated body portion 110 can further include at least one exit port at proximal end 112 to dispel a product. In some embodiments, proximal end 112 can include one, two, three, four, five, six, seven, eight, nine, ten, eleven, twelve, thirteen, fourteen, or fifteen exit ports. For example, elongated body portion 110 can include a single exit port, exit port 122.

Figure 2:
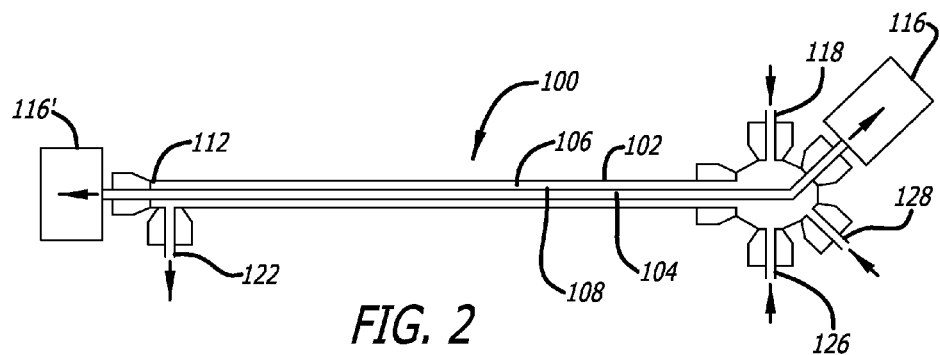
FIG. 2 illustrates an example tube-in-tube reactor with two sites for substrate(s)s delivery.
Figure 3:
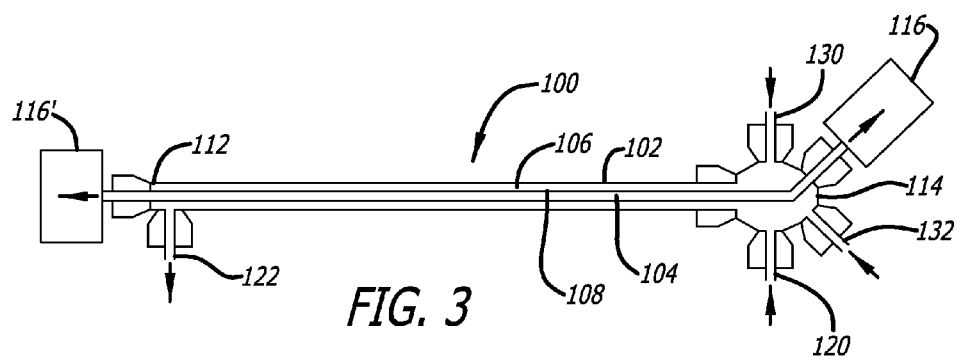
FIG. 3 illustrates an example tube-in-tube reactor with two sites for catalyst delivery.

Substrate(s) and optionally catalyst(s) can be delivered to a mixing or reaction zone 124. For example, in FIGS. 1A and 1B, substrate(s) and catalyst(s) can be delivered to reaction zone 124 in two streams. In other embodiments, substrate(s) can be delivered by two or more streams. For example, as illustrated in FIG. 2, tube-in-tube reactor 100 includes first substrate port 126 and second substrate port 128. In still other embodiments, catalyst(s) can be delivered by two or more streams. For example, as illustrated in FIG. 3, tube-in-tube reactor 100 can include first catalyst port 130 and second catalyst port 132.

Figure 4:
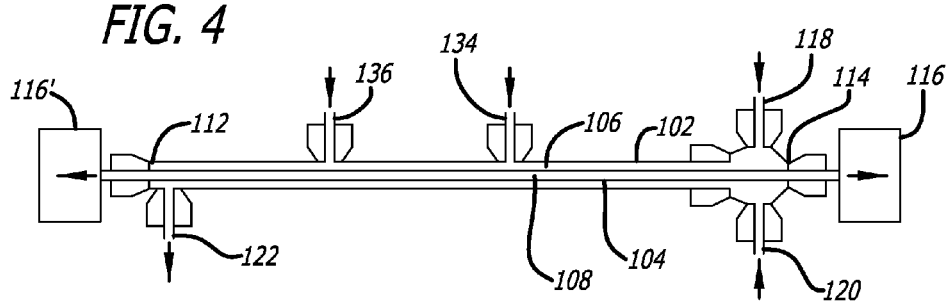
FIG. 4 illustrates an example tube-in-tube reactor designed for delivery of catalyst(s) in portions.

In some embodiments, catalyst(s) can be delivered in one or more portions to one or more different ports along outer impermeable tube 102 of tube-in-tube reactor 100 as illustrated in FIG. 4. In some embodiments, outer impermeable tube 102 can include one, two, three, four, five, six, seven, eight, nine, ten, eleven, twelve, thirteen, fourteen, or fifteen catalyst ports along its length. These ports can be evenly spaced along outer impermeable tube 102 or can be randomly spaced along outer impermeable tube 102. In one embodiment, tube-in-tube reactor 100 can include first spaced catalyst port 134 and second spaced catalyst port 136 to disperse catalyst along outer impermeable tube 102.

In some embodiments, substrates can be delivered in one or more portions to one or more different ports along outer impermeable tube 102 of tube-in-tube reactor 100. In some embodiments, outer impermeable tube 102 can include one, two, three, four, five, six, seven, eight, nine, ten, eleven, twelve, thirteen, fourteen, or fifteen substrate ports along its length. These ports can be evenly spaced along outer impermeable tube 102 or can be randomly spaced along outer impermeable tube 102.

Figure 5:
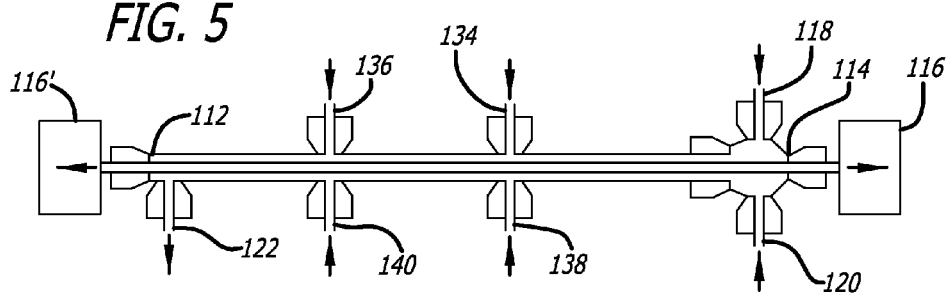
FIG. 5 illustrates an example tube-in-tube reactor designed for delivery of catalyst(s) and substrate(s) in portions.

In one embodiment, tube-in-tube reactor 100 can include combinations of catalyst and substrate ports along outer impermeable tube 102 as shown on FIG. 5. Such a reactor can be useful in reactions in which the substrate's concentration in the reaction mixture needs to be maintained at low level. For example, in one embodiment, tube-in-tube reactor 100 can include first spaced catalyst port 134 and second spaced catalyst port 136 as well as first spaced substrate port 138 and second spaced catalyst port 140.

Figure 6A:
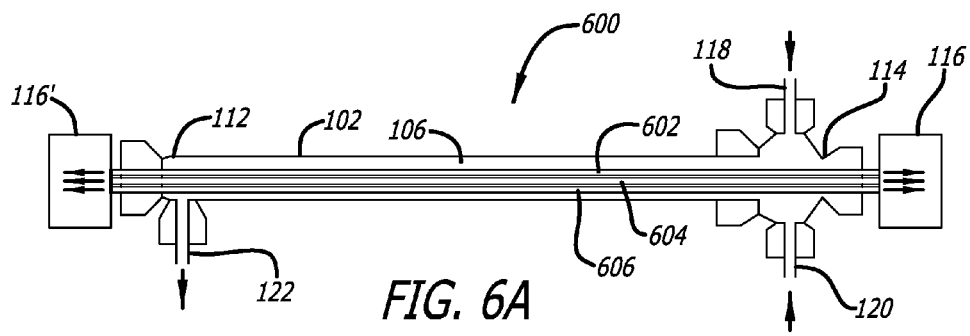
FIG. 6A illustrates a schematic presentation of a tube-in-tube reactor with several inner semi-permeable tubes.
Figure 6B:
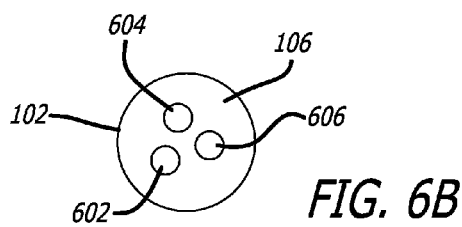
FIG. 6B illustrates a cross section of the tube-in-tub reactor of FIG. 6A.

In some embodiments, a tube-in-tube reactor can include multiple inner, semi-permeable tubes. A tube-in-tube reactor can include any number of inner semi-permeable tubes that may be required to achieve described reaction characteristics or that can fit within an outer reaction tube. A tube-in-tube reactor can include two, three, four, five, six, seven, eight, nine, ten, eleven, twelve, thirteen, fourteen, or fifteen inner-semi-permeable tubes. FIGS. 6A and 6B illustrates an example tube-in-tube reactor 600 including three inner semi-permeable tubes, first inner semi-permeable tube 602, second inner semi-permeable tube 604, and third inner semi-permeable tube 606. Such a multi-inner-semi-permeable tube configuration may be beneficial for industrial production of products and removal of by-products.

The conceptions of tube-in-tube reactor design presented on FIGS. 1-6 are not limiting. Generally the number and places of connection of tubes that deliver catalyst(s) and/or substrate(s) as well as number and places of connection of inner, semi-permeable tubes are almost unlimited and depend on the user's needs.

Figure 7A:
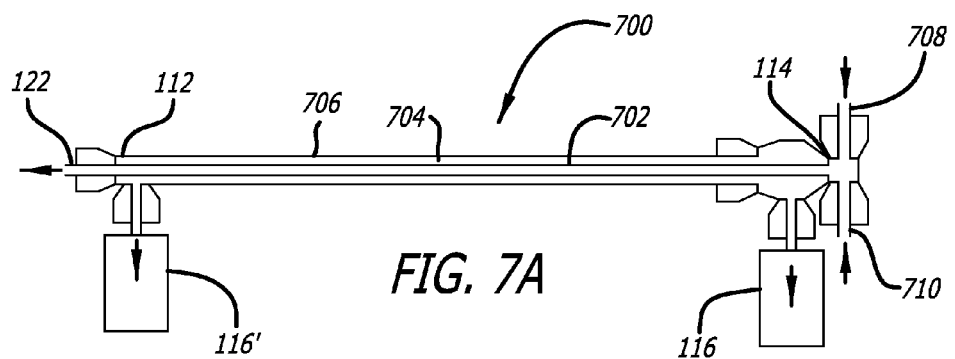
FIG. 7A illustrates an example tube-in-tube reactor designed for running metathesis reaction in inner semi-permeable tube.
Figure 7B:
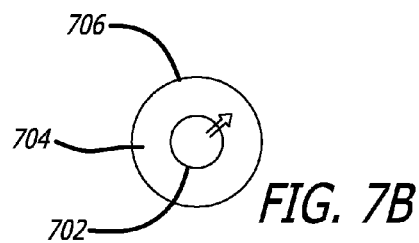
FIG. 7B illustrates a cross section of the tube-in-tub reactor of FIG. 7A.

In some embodiments, an oppositely configured tube-in-tube reactor is envisioned. Such a reactor, tube-in-tube reactor 700 is illustrated in FIGS. 7A and 7B. A metathesis reaction can occur in inner semi-permeable tube 702. Vacuum can be generated in space 704 between inner semi-permeable tube 702 and outer tube 706 as shown in FIGS. 7A and 7B. Tube-in-tube reactor 700 includes catalyst port 708 and substrate port 710 which are operably connected to inner semi-permeable tube 702.

In some embodiments, metathesis reactions can be promoted by one or more heterogeneous catalyst. The suitable heterogeneous catalyst can be loaded into the inner semi-permeable tube or into the space between the inner semi-permeable tube and the outer, impermeable tube. In either case, solutions of substrate(s) and optionally homogeneous catalysts can be passed through a bed of heterogeneous catalyst. The appropriate tube is joined with one or more vacuum pump to facilitate removal of ethylene.

Figure 8A:
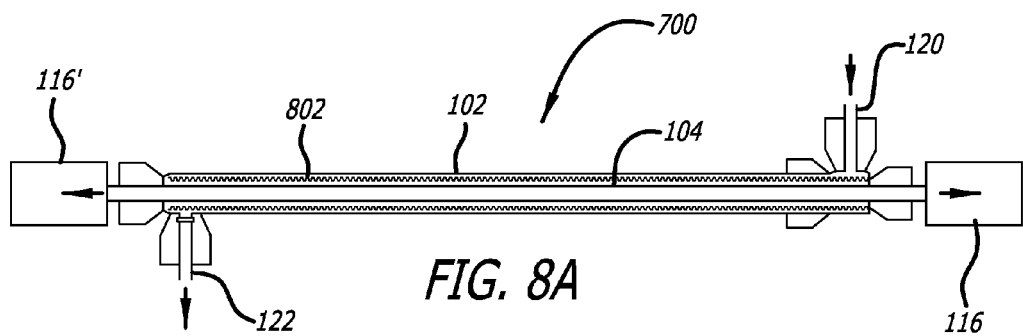
FIG. 8A illustrates a schematic diagram of reactor in which a heterogeneous catalyst is loaded into the space between inner and outer tube.
Figure 8B:
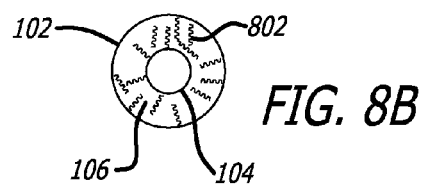
FIG. 8B illustrates a cross section of the tube-in-tub reactor of FIG. 8A.

As illustrated in FIGS. 8A and 8B, tube-in-tube reactor 800 includes outer impermeable tube 102 and inner tube 104 made from a semi-permeable material. Tube-in-tube reactor 800 houses heterogeneous catalyst 802 within first reaction chamber 106 and inner tube 104 is connected to a vacuum source 116 to remove ethylene.

Figure 9A:
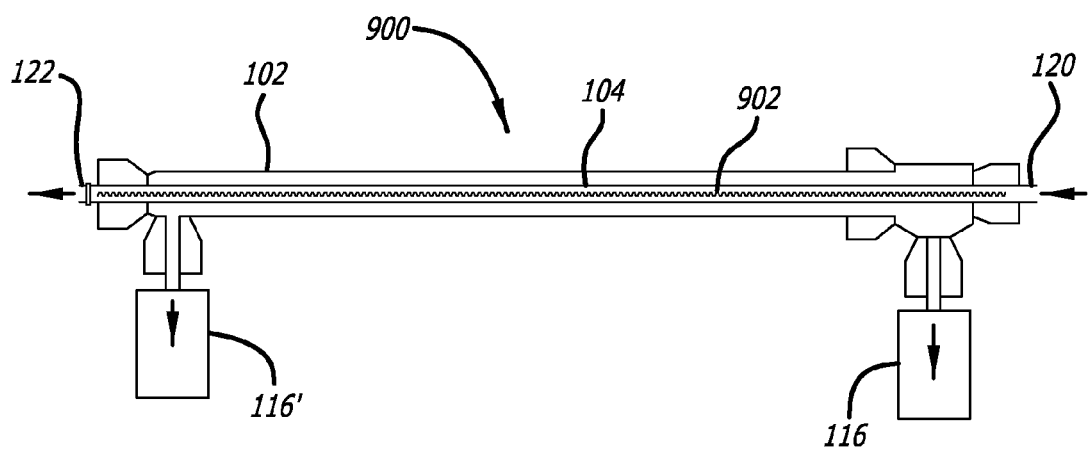
FIG. 9A illustrates a schematic diagram of reactor in which a heterogeneous catalyst is loaded into inner tube.
Figure 9B:
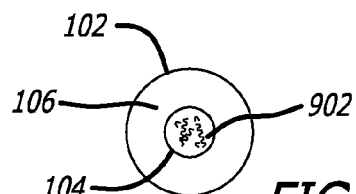
FIG. 9B illustrates a cross section of the tube-in-tub reactor of FIG. 9A.

As illustrated in FIGS. 9A and 9B, tube-in-tube reactor 900 includes outer tube 102 and inner semi-permeable tube 104. Tube-in-tube reactor 900 houses heterogeneous catalyst 902 within inner semi-permeable tube 104 and outer tube 102 is connected to a vacuum source 116 to remove ethylene.

When a heterogeneous catalyst is used, it can fill at least a portion of the reaction zone, such as about 1%, about 5%, about 10%, about 20%, about 30%, about 40%, about 50%, about 60%, about 70%, about 80%, about 90%, about 95%, about 100%, between about 5% and about 99%, between about 5% and about 75%, between about 50% and about 99%, at least about 25%, at least about 50%, at least about 75% of the reaction zone.

A stream of substrate(s) or its/their solution(s) and solution(s) of catalyst(s) can be joined and mixed for example in T or Y type junction or other type of mixer. This junction or mixer can be directly connected to the tube-in-tube reactor or in suitable mixer indirectly joined with tube-in-tube reactor. The mixer as well as the stream of substrate(s) or its/their solution(s) and solution(s) of catalyst(s) can be heated or cooled as desired.

The tube-in-tube reactor can have an outer tube having an inner diameter of about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm, between about 1.1 mm and about 2.0 mm, between about 1.4 mm and about 1.6 mm, or a range formed between any two of these values. The tube-in-tube reactor can have an outer tube having an outer diameter of about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, or about 3.5 mm, between about 2.5 mm and about 3.5 mm, between about 2.9 mm and about 3.1 mm, or a range formed between any two of these values. The inner tube can have an outer diameter of about 0.8 mm, about 0.9 mm, about 1.0 mm, 1.2 mm, about 1.3 mm, about 1.4 mm, or about 1.5 mm, between about 0.8 mm and about 1.5 mm, between about 0.9 mm and about 1.1 mm, or a range formed between any two of these values. Inner tube can have internal diameter of about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, or about 1.2 mm, between about 0.2 mm and about 1.2 mm, between about 0.7 mm and about 0.9 mm, or a range formed between any two of these values. In one embodiment, the tube-in-tube reactor can have a relatively small diameter. The tube-in-tube reactor can have a length of about 0.5 m, about 0.6 m, about 0.7 m, about 0.8 m, about 0.9 m, about 1.0 m, about 1.2 m, about 1.3 m, about 1.4 m, about 1.5 m, about 1.6 m, about 1.7 m, about 1.8 m, about 1.9 m, or about 2.0 m, about 2.1 m, about 2.2 m, about 2.3 m, about 2.4 m, or about 2.5 m, between about 0.5 m and about 2.5 m, or a range formed between any two of these values. In one embodiment, the tube-in-tube reactor can be relatively short. Such a tube-in-tube reactor can be used for production purposes as well as for laboratory research.

For industrial production uses, a tube-in-tube reactor can be much larger in scale. A large scale tube-in-tube reactor can have an outer tube having an outer diameter of about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, about 2.5 cm, about 2.6 cm, about 2.7 cm, about 2.8 cm, about 2.9 cm, about 3.0 cm, about 3.1 cm, about 3.2 cm, about 3.3 cm, about 3.4 cm, about 3.5 mm, about 4.0 cm, about 4.5 cm, about 5 cm, about 6 cm, about 7 cm, about 8 cm, about 9 cm, or about 10 cm, between about 1.1 cm and about 10 cm, between about 1 cm and about 10 cm, or a range formed between any two of these values. The inner diameter of the outer tube can be diameter of about 1.1 cm, about 1.2 cm, about 1.3 cm, about 1.4 cm, about 1.5 cm, about 1.6 cm, about 1.7 cm, about 1.8 cm, about 1.9 cm, or about 2.0 cm, about 2.1 cm, about 2.2 cm, about 2.3 cm, about 2.4 cm, about 2.5 cm, about 2.6 cm, about 2.7 cm, about 2.8 cm, about 2.9 cm, about 3.0 cm, about 3.1 cm, about 3.2 cm, about 3.3 cm, about 3.4 cm, or about 3.5 cm, between about 1.1 cm and about 3.5 cm, or a range formed between any two of these values. The inner tube can have an outer diameter and inner diameter that compliments to size of the outer tube. The tube-in-tube reactor can have a length of about 1 m, about 5 m, about 10 m, about 20 m, about 30 m, about 40 m, 50 m, about 60 m, about 70 m, about 80 m, about 90 m, about 100 m, about 110 m, about 120 m, or about 140 m, about 160 m, about 180 m, about 200 m, about 250 m, or about 300 m, between abut 1 m and about 300 m, between about 50 m and 150 m, or a range formed between any two of these values. In one embodiment, the tube-in-tube reactor can be relatively large.

In other embodiments, a short reactor with large diameter as well as long reactor with small diameter can be also applied.

The tube-in-tube reactor can be applied for running of any kind of olefin metathesis reaction that proceed with evolution of by-products such as, but not limited to, ethylene and/or acetylene.

Conditions for olefin metathesis can be as follows. A reaction can be run at concentration as low as 0.001 M or can be run in neat substrate. The temperature of a reaction can be about 0° C., about 10° C., about 20° C., about 30° C., about 40° C., about 50° C., about 60° C., about 70° C., about 80° C., about 90° C., about 100° C., about 110° C., about 120° C., about 130° C., about 140° C., about 150° C., or between about 0° C. and about 150° C. Depending on the substrate(s) nature the catalyst(s) loading can be between 2 and several thousands of ppm.

In some embodiments, the tube-in-tube reactor can be placed in microwave oven and the reaction mixture can be heated using microwave irradiation. In some embodiments, microwave irradiation can for some metathetical transformations give superior results compared to traditional heating.

In some embodiments, the impurities containing ruthenium are removed on-line. This can be realized by connection of the tube-in-tube reactor with a set-up equipped with appropriate membrane designed for filtration of metathesis catalysts and/or their decomposition products. Residual ruthenium can be also removed on-line by quenching the post-reaction mixture with an appropriate ruthenium scavenger and subsequent application of suitable purification technique, such as: biphasic extraction or driving of quenched reaction mixture though the bed of adequate absorbent (eg. silica gel, aluminum oxide). Alternatively, the post-reaction mixture can be simply passed through the bed of solid ruthenium scavenger or activated carbon in order to remove ruthenium containing impurities.

EXAMPLES

Toluene was dried by distillation over Na, transferred under argon and stored over MS 4A. Indenylidene second generation catalyst 3 as well as nitro-substituted Hoveyda catalyst 2' and catalyst 6 were attained.

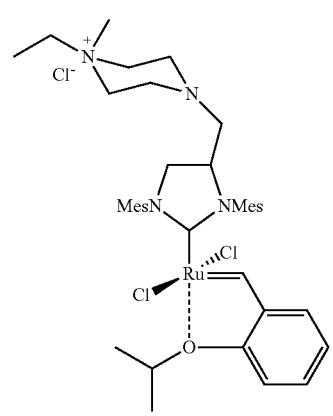

Teflon AF2400 tubing was purchased from Biogeneral. Fine Teflon, impermeable tubes were purchased from Postnova. Column chromatography was performed on Merck silica gel 60 (230-400 mesh).

Analytical Methods

NMR: Spectra were recorded on a Bruker Avance 300 MHz spectrometer in $CDCl_3$; chemical shifts (δ) were reported in parts per million (ppm) downfield from trimethylsilane as referenced to residual protio solvent peaks, coupling constants (J) in Hz.

GC: Trace GC Ultra, Thermo Electron Corporation, HP-5 column; inlet temperature 250° C.; detector temperature 300° C. Retention times were confirmed with samples authenticated by NMR analysis. Residual ruthenium was measured using ICP-MS method.

Method parameters for RCM of 7: initial temperature 170° C., initial time 1 min, ramp 12° C./min, final temperature 240, final time 1 min; retention times: substrate 6.161 min, product 8 6.750 min.

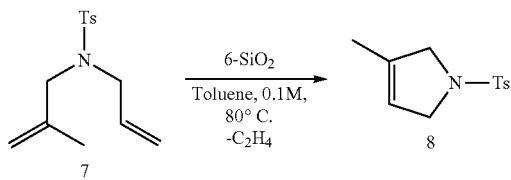 [SMILES: C=CCN(CC(=C)C)S(=O)(=O)c1ccc(C)cc1 ; CC1=CCN(S(=O)(=O)c2ccc(C)cc2)C1]

Method parameters for RCM of 9: initial temperature 160° C., initial time 1 min, ramp 10° C./min, final temperature 220, final time 1 min; retention times: substrate 3.471 min, product 10 3.065 min.

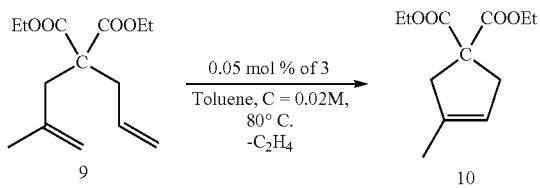 [SMILES: C=CCC(CC(=C)C)(C(=O)OCC)C(=O)OCC ; CCOC(=O)C1(C(=O)OCC)CC=C(C)C1]

Method parameters for RCM of 11: initial temperature 172° C., initial time 0.1 min, ramp 6.5° C./min, final temperature 210, final time 1.0 min; retention times: substrate 5.801 min, product 13 (E isomer 5.728 min, Z isomer 5.876 min), dodecane 1.840 min. Method parameters for RCM of 12: initial temperature 160° C., initial time 0.1 min, ramp 6° C./min, final temperature 210, final time 1.0 min; retention times: substrate 5.023 min, product 14 (E isomer 4.943 min, Z isomer 5.105 min), dodecane 2.062 min.

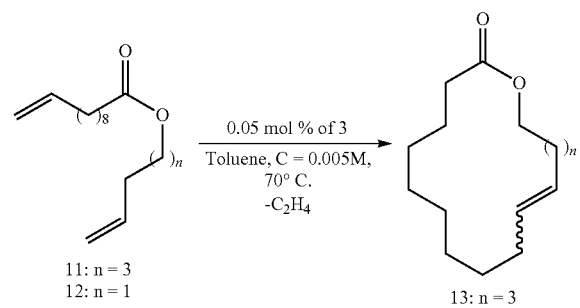

Method parameters for CM of 15 with 16: initial temperature 170° C., initial time 0.1 min, ramp 8° C./min, second temperature 195° C., second time 0.1 min, ramp 50° C./min, final temperature 295° C., final time 4 min; retention times: substrate 15 2.501 min, product 17 (E isomer 4.370 min, Z isomer 4.175 min), dimer of 15 6.400 min.

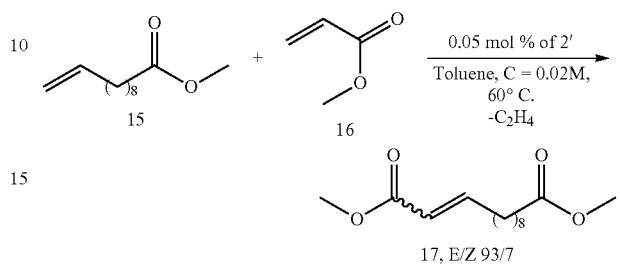

Equipment for CF Experiments with Heterogeneous Catalyst:

tube-in-tube reactor: length—40 cm; outer tube—ID=1.57 mm, OD=3.15 mm, inner tube—ID=0.8 mm, OD=1 mm. Solution of 7 was driven through the system with the use of PN 1610 Syringe Dosing System (Postnova). A schematic diagram of the reactor used in these experiments is illustrated in FIG. 8.

Equipment for CF Experiments with Homogeneous Catalyst:

tube-in-tube reactor length: 2 m; outer tube—ID=1.57 mm, OD=3.15 mm, inner tube—ID=0.8 mm, OD=1 mm. Solutions of substrate(s) and catalyst were driven through the system with the use of AP23 double syringe pump (ascor). No special mixer was used for mixing the substrate(s) and catalyst streams. Schematic diagram of the reactor used in these experiments is illustrated in FIG. 1.

Construction of Time Profile for Homogeneous Reactions in PFR and PFR-V:

Reaction times were varied by controlling the flow rates through the system. Each data-point in the rate curves corresponds to a separate experiment. Flow rates were in the range of 4-48 mL/h. For each, a 1 min interval was allowed for the new flow rate to stabilize, followed by purging for doubled reaction time prior to collecting samples for analysis. Samples for GC were collected to the vial already containing ethyl vinyl ether to ensure immediate quenching of the reaction.

Stock Solutions Used in the Course of Research:

Stock Solution A:

N-Tosyl allylmethallylamine (7) (4.50 g, 16.96 mmol) was placed in a dry flask under argon and dry, degassed toluene (166 mL) was added so that the final concentration of reagent was 0.1 M.

Stock Solution B:

Diethyl allylmethallylmalonate (9) (5.00 g, 19.66 mmol) was placed in a dry flask under argon and dry, degassed toluene (44.3 mL) was added so that the final concentration of reagent was 0.4 M.

Stock Solution C:

Diethyl allylmethallylmalonate (0.87 g, 3.42 mmol) was placed in a dry flask under argon and dry, degassed toluene (85 mL) was added so that the final concentration of reagent was 0.04 M.

Stock Solution D:

Hex-5-en-1-yl-undec-10-enoate (11) (1.737 g, 6.52 mmol) and dodecane (1.111 g, 6.52 mmol) were placed in a dry flask under argon. To this mixture dry, degassed toluene (650 mL) was added so that the final concentration of reagent and internal standard was 0.01 M.

Stock Solution E:

But-3-en-1-yl-undec-10-enoate (12) (0.496 g, 2.08 mmol) and dodecane (0.354 g, 2.08 mmol) were placed in a dry flask under argon. To this mixture dry, degassed toluene (207 mL) was added so that the final concentration of reagent and internal standard was 0.01 M.

Stock Solution F:

Indenylidene second generation catalyst (3) (10 mg, 10.53 µmol) was dissolved under argon in dry, degassed toluene (1000 µL).

Stock Solution G:

Methyl-undec-10-enoate (15) (10.00 g, 50.4 mmol) and methyl acrylate (16) (16) (17.37 g, 202 mmol, 4 eq) were placed in a dry flask under argon. To this mixture dry, degassed toluene (96.4 mL) was added so that the final concentration of methyl undec-10-enoate was 0.4 M.

Stock Solution H:

Methyl-undec-10-enoate (15) (1.00 g, 5.0 mmol) and methyl acrylate (16) (1.74 g, 20.2 mmol, 4 eq) were placed in a dry flask under argon. To this mixture dry, degassed toluene (123 mL) was added so that the final concentration of methyl undec-10-enoate was 0.04 M.

Stock Solution I:

Nitro-Grela catalyst (2') (10 mg, 15 µmol) was dissolved under argon in dry, degassed toluene (1000 µL).

Example 1

Preparation of 6-SiO$_2$ for Reactions in BR PFR and PFR-V

Complex 6 (6 mg, 7.46 µmol) was dissolved in DCM (4 mL) and silica gel (234 mg) was added. The resulting suspension was stirred at room temperature for 2 minutes. Next, solvent was removed on a rotavapor to give 6-SiO$_2$ (240 mg) which was dried on high vacuum for 10 minutes prior to use.

Example 2

RCM of 7 in BR

Stock solution A (38 mL, 3.80 mmol of 7) was stabilized at 80° C. and 6-SiO$_2$ (240 mg, 7.60 µmol of 6, 0.2 mol %) was added in one portion and the reaction was stirred at 700 rpm. Reaction progress was monitored by GC-FID (100 µL of reaction mixture was removed periodically, filtered through cotton and diluted with 450 µL of toluene). The results are summarized in Table 1. Residual ruthenium in the product was determined to be 3.2 ppm.

TABLE 1

RCM of 7 in BR.

| Time [min] | Conversion [%] |
| --- | --- |
| 2 | 30 |
| 4 | 68 |
| 6 | 84 |
| 8 | 90 |
| 10 | 93 |
| 15 | 96 |
| 20 | 98 |
| 30 | 98 |

Example 3

Split Test for RCM of 7 in BR

The RCM of 7 promoted by 6-SiO$_2$ was carried out as described above. Half of the reaction mixture was filtered after 3 minutes of reaction through a piece of cotton (under argon) to the new flask that was filled with argon and placed in an oil bath heated to 80° C. The filtered mixture was immediately analysed by GC-FID in order to determine the conversion at the split time (50%). After 30 minutes, conversion in filtered and non-filtered reaction mixtures was determined by GC-FID to be 50 and 98%, respectively.

Example 4

RCM of 7 in PFR

A sample of 6-SiO$_2$ (240 mg, 7.60 µmol of 6) was loaded into a tube-in tube reactor (in which both outlets of inner tube were closed; PFR) as a suspension in dry, degassed toluene and additional 4 mL of solvent was passed through the reactor. Next, the reactor was connected with a tube that delivered a solution of substrate (previously filled with stock solution A) and placed in an oil bath heated to 80° C. Stock solution A (large excess) was placed in a round bottom, two-necked flask from which it was transferred into the reactor with the use of a Syringe Dosing System with a flow rate of 0.04 mL/min via a tube (ID 1.0 mm, OD 1.57 mm) placed in the oil bath heated to 80° C. Periodically, reaction mixture samples (40 µL) were collected, diluted with toluene (200 µL), and analysed by GC-FID to determine conversion. After 20 h all samples collected for GC analysis were joined with the main fraction and overall conversion was determined by GC-FID to be 11% what corresponds to the TON of 71. Residual ruthenium in the product was determined to be 1.5 ppm.

Example 5

RCM of 7 in PFR-V

A sample of 6-SiO$_2$ (240 mg, 7.60 µmol of 6) was loaded into a tube-in tube reactor (in which both outlets of inner tube were connected with vacuum pump; PFR-V) as a suspension in dry, degassed toluene and additional 4 mL of solvent was passed through the reactor. From this point, the procedure was identical as for reaction in PFR. After 20 h, all samples collected for GC analysis and a sample from split test were joined with the main fraction and overall conversion was determined by GC-FID to be 24% what corresponds to the TON of 154. Residual ruthenium in the product was determined to be 3.0 ppm.

Example 6

Split Test for RCM of 7 in PFR-V

RCM of 7 was run as described above and after 160 minutes, the reaction mixture sample (200 µL) was collected into a 5 mL flask prefilled with argon; 40 µL of this mixture was transferred to GC vial, quenched with ethyl vinyl ether (4 µL), diluted with toluene (200 µL), and analysed by GC-FID to determine conversion at split time (43%). The remainder of sample was gently stirred at 80° C. for additional 200 minutes. After that sample for GC was prepared and analysed—conversion was determined to be 43%.

The results of RCM of 7 in flow mode are collected in Table 2.

TABLE 2

RCM of 7 in CF mode.

| Time [min] | Conversion [%] | |
|---|---|---|
| | PFR-V | PFR |
| 20 | 100 | 100 |
| 40 | 100 | 84 |
| 60 | 98 | 46 |
| 80 | 89 | 33 |
| 100 | 73 | 28 |
| 120 | 58 | 24 |
| 140 | 48 | 23 |
| 160 | 43 | 22 |
| 180 | 39 | 20 |
| 200 | 35 | 17 |
| 220 | 33 | 16 |
| 240 | 31 | 15 |
| 260 | 29 | 13 |
| 280 | 27 | 12 |
| 300 | 25 | 11 |
| 360 | 21 | 10 |
| 420 | 20 | 8 |
| 1200 | 10 | 1 |

Example 7

RCM of 9 in BR (0.2 M Reaction Concentration)

Stock solution B (5 mL) was placed in a dry flask, diluted with dry, degassed toluene (5 mL), and the resulting solution (0.2 M) was stabilized at 80° C. Next, stock solution F (95 µL) was added and reaction progress was monitored by GC-FID (100 µL of reaction mixture was removed periodically, quenched with 4 µL of ethyl vinyl ether and diluted with 900 µL of toluene).

Example 8

RCM of 9 in PFR (0.2 M Reaction Concentration)

A syringe was filled with stock solution B (25 mL) and installed in syringe pump. Stock solution F (475 µL) was placed in a dry flask and diluted with dry, degassed toluene (24.5 mL). The syringe was filled with the resulting solution and installed in the syringe pump. Solutions were pumped with the same speed (to give the final reaction concentration of 0.2 M) into PFR placed in oil bath heated to 80° C. The stock solution B was delivered through a tube placed in the same oil bath. Reaction progress was monitored by GC-FID (100 µL of reaction mixture was collected, quenched with 4 µL of ethyl vinyl ether and diluted with 900 µL of toluene).

Example 9

RCM of 9 in PFR-V (0.2 M Reaction Concentration)

A reaction was carried out and monitored as described for PFR with the use of PFR-V in which an internal tube was connected with the high vacuum pump (pressure was in the range of 0.05-0.07 mbar).

Example 10

RCM of 9 in BR (0.02 M Reaction Concentration)

Stock solution C (10 mL) was placed in a dry flask, diluted with dry, degassed toluene (10 mL), and the resulting solution (0.02 M) was stabilized at 80° C. Next, stock solution F (19 µL) was added, and reaction progress was monitored by GC-FID (200 µL of reaction mixture was removed periodically, quenched with 4 µL of ethyl vinyl ether and analysed at this concentration).

Example 11

RCM of 9 in PFR (0.02 M Reaction Concentration)

A syringe was filled with stock solution C (25 mL) and installed in a syringe pump. Stock solution F (48 µL) was placed in a dry flask and diluted with dry, degassed toluene (25 mL). The syringe was filled with the resulting solution and installed in the syringe pump. Solutions were pumped with the same speed (to give the final reaction concentration of 0.02 M) into a PFR placed in oil bath heated to 80° C. The stock solution C was delivered through a tube placed in the same oil bath. Reaction progress was monitored by GC-FID (200 µL of reaction mixture was collected, quenched with 4 µL of ethyl vinyl ether and analysed at this concentration).

Example 12

RCM of 9 in PFR-V (0.02 M Reaction Concentration)

A reaction was carried out and monitored as described for PFR with the use of PFR-V in which the internal tube was connected with a high vacuum pump (pressure was in the range of 0.05-0.07 mbar).

The results of RCM of 9 are collected in Table 3 and Table 4.

TABLE 3

RCM of 9 at 0.2M concentration.

| Entry | Flow rate [mL/h] | Reaction time [min] | Conversion [%] | | |
|---|---|---|---|---|---|
| | | | BR | PFR-V | PFR |
| 1 | 24 | 5 | 66 | 63 | 61 |
| 2 | 12 | 10 | 87 | 80 | 77 |
| 3 | 8 | 15 | 91 | 90 | 83 |
| 4 | 6 | 20 | 92 | 91 | 83 |
| 5 | 4 | 30 | 92 | 91 | 83 |

TABLE 4

RCM of 9 at 0.02M concentration

| Entry | Flow rate [mL/h] | Reaction time [min] | Conversion [%] | | |
|---|---|---|---|---|---|
| | | | BR | PFR-V | PFR |
| 1 | 24 | 5 | 60 | 83 | 71 |
| 2 | 12 | 10 | 87 | 95 | 83 |
| 3 | 8 | 15 | 93 | 97 | 83 |
| 4 | 6 | 20 | 95 | 98 | 83 |
| 5 | 4 | 30 | 95 | 98 | 83 |

Example 13

RCM of 11 in BR

Stock solution D (18 mL) was placed in a dry flask, diluted with dry, degassed toluene (18 mL), and 150 µL of this solution was removed and analysed by GC-FID to establish the initial ratio between the substrate and dodecane at $t_0$ (0% conversion). The remaining substrate solution (0.005 M) was stabilized at 80° C. and stock solution F (86 μL, 0.5 mol % of catalyst) was added. Reaction progress was monitored by GC-FID (200 μL of reaction mixture was removed periodically, quenched with 4 μL of ethyl vinyl ether and analysed at this concentration).

Example 14

RCM of 11 in PFR

A syringe was filled with stock solution D (25 mL) and installed in a syringe pump. Stock solution F (119 μL) was placed in a dry flask and diluted with dry, degassed toluene (24.9 mL). The syringe was filled with the resulting solution and installed in the syringe pump. Solutions were pumped at the same speed (to give the final substrate concentration of 0.005 M) into PFR placed in oil bath heated to 70° C. The stock solution D was delivered through a tube placed in the same oil bath. Reaction progress was monitored by GC-FID (200 μL of reaction mixture was collected, quenched with 4 μL of ethyl vinyl ether and analysed at this concentration). The initial ratio of substrate to dodecane determined for RCM of 11 in BR was used for calculations in this experiment.

Example 15

RCM of 11 in PFR-V

A reaction was carried out and monitored as described for PFR with the use of PFR-V in which the internal tube was connected with a high vacuum pump (pressure was in the range of 0.05-0.07 mbar).

The selectivity of the RCM of 11 was affected only by ring contracted and isomerized by-products and not by oligomerization.

The results of RCM of 11 are collected in Table 5.

TABLE 5

Macrocyclization of 11.

| Entry | Flow rate [mL/h] | Reaction time [min] | Conversion (Selectivity) [%] | | | Yield [%][a] | | |
|---|---|---|---|---|---|---|---|---|
| | | | BR | PFR-V | PFR | BR | PFR-V | PFR |
| 1 | 12 | 10 | 69 (91) | 64 (96) | 47 (98) | 63 | 61 | 46 |
| 2 | 8 | 15 | 78 (90) | 83 (95) | 51 (97) | 78 | 79 | 50 |
| 3 | 6 | 20 | 91 (90) | 91 (95) | 59 (97) | 81 | 86 | 57 |
| 4 | 4 | 30 | 93 (90) | 96 (94) | 59 (97) | 84 | 90 | 57 |

[a]final E/Z ratio = 8/2 in all cases

Example 16

RCM of 11 in PFR-V Promoted by 0.25 Mol % of Catalyst 3

A syringe was filled with stock solution D (25 mL) and installed in a syringe pump. Stock solution F (59 μL) was placed in a dry flask and diluted with dry, degassed toluene (25 mL). The syringe was filled with the resulting solution and installed in the syringe pump. Solutions were pumped at the same speed (to give the final substrate concentration of 0.005 M) into PFR-V placed in oil bath heated to 70° C. The stock solution D was delivered through a tube placed in the same oil bath. Reaction progress was monitored by GC-FID (200 μL of reaction mixture was collected, quenched with 4 μL of ethyl vinyl ether and analysed at this concentration). The initial ratio of substrate to dodecane determined for experiment in BR was used for calculations in this experiment. Maximum conversion of 62% was reached after 20 minutes of reaction (96% of selectivity, 60% of yield).

Example 17

RCM of 12 in BR

A stock solution E (18 mL) was placed in a dry flask, diluted with dry, degassed toluene (18 mL), and 150 μL of this solution was removed and analysed by GC-FID to establish the initial ratio between the substrate and dodecane at $t_0$ (0% conversion). The remaining substrate solution (0.005 M) was stabilized at 70° C. and stock solution F (86 μL, 0.5 mol % of catalyst) was added. Reaction progress was monitored by GC-FID (200 μL of reaction mixture was removed periodically, quenched with 4 μL of ethyl vinyl ether and analysed at this concentration).

Example 18

RCM of 12 in PFR

A syringe was filled with stock solution E (25 mL) and installed in a syringe pump. Stock solution F (119 μL) was placed in a dry flask and diluted with dry, degassed toluene (25 mL). The syringe was filled with the resulting solution and installed in the syringe pump. Solutions were pumped at the same speed (to give the final substrate concentration of 0.005 M) into PFR placed in oil bath heated to 70° C. Stock solution E was delivered through a tube placed in the same oil bath. Reaction progress was monitored by GC-FID (200 μL of reaction mixture was collected, quenched with 4 μL of ethyl vinyl ether and analysed at this concentration). The initial ratio of substrate to dodecane determined for RCM of 12 in BR was used for calculations in this experiment.

Example 19

RCM of 12 in PFR-V

A reaction was carried out and monitored as described for PFR with the use of PFR-V in which internal tube was connected with a high vacuum pump (pressure was in the range of 0.05-0.07 mbar).

The selectivity of RCM of 12 was affected only by ring contracted and isomerized by-products and not by oligomerization.

The results of RCM of 12 are collected in Table 6.

TABLE 6

RCM of 12.

| Entry | Flow rate [mL/h] | Reaction time [min] | Conversion (Selectivity) [%] | | | Yield [%][a] | | |
|---|---|---|---|---|---|---|---|---|
| | | | BR | PFR-V | PFR | BR | PFR-V | PFR |
| 1 | 12 | 10 | 56 (99) | 61 (98) | 40 (99) | 55 | 60 | 40 |
| 2 | 8 | 15 | 73 (98) | 77 (99) | 47 (99) | 72 | 76 | 47 |
| 3 | 6 | 20 | 82 (98) | 86 (99) | 52 (99) | 80 | 85 | 52 |
| 4 | 4 | 30 | 87 (97) | 93 (98) | 60 (98) | 84 | 91 | 59 |

[a]final E/Z ratio = 9/1 in all cases

Example 20

CM of 15 and 16 at 0.2 M Concentration in BR

Stock solution G (10 mL) was placed in a dry flask, diluted with dry, degassed toluene (10 mL), and the resulted solution (0.2 M) was stabilized at 60° C. Next, a solid catalyst 2' (13 mg, 0.5 mol %) was added and the reaction progress was monitored by GC-FID (100 μL of reaction mixture was removed periodically, quenched with 4 μL of ethyl vinyl ether and diluted with 900 μL of toluene).

Example 21

CM of 15 and 16 at 0.2 M Concentration in PFR

A syringe was filled with stock solution G (25 mL) and installed in a syringe pump. Solid catalyst 2' (34 mg, 0.5 mol %) was dissolved in dry, degassed toluene (25 mL) and the resulting solution was transferred to the syringe which was then installed in a syringe pump. Solutions were pumped at the same speed (to give final substrate concentration of 0.2 M) into PFR placed in oil bath heated to 60° C. Stock solution G was delivered through a tube placed in the same oil bath. Reaction progress was monitored by GC-FID (100 μL of reaction mixture was collected, quenched with 4 μL of ethyl vinyl ether, and diluted with 900 μL of toluene).

Example 22

CM of 15 and 16 at 0.2 M Concentration in PFR-V

A reaction was carried out and monitored as described for PFR with the use of PFR-V in which internal tube was connected with the high vacuum pump (pressure was in the range of 0.05-0.07 mbar).

Example 23

CM of 15 and 16 at 0.02 M in BR

Stock solution H (10 mL) was placed in a dry flask, diluted with dry, degassed toluene (10 mL), and stabilized at 60° C. and stock solution I (135 μL, 0.5 mol %) was added. Reaction progress was monitored by GC-FID (200 μL of reaction mixture was removed periodically, quenched with 4 μL of ethyl vinyl ether and analysed at this concentration).

Example 24

CM of 15 and 16 at 0.02 M Concentration in PFR

A syringe was filled with stock solution H (25 mL) and installed in a syringe pump. Stock solution I (336 μL) was placed in a dry flask and solvent was removed. Next, a catalyst was dissolved in dry, degassed toluene (25 mL). The syringe was filled with the resulting solution and installed in a syringe pump. Solutions were pumped at the same speed (to give the final substrate concentration of 0.02 M) into PFR placed in oil bath heated to 60° C. Stock solution H was delivered through a tube placed in the same oil bath. Reaction progress was monitored by GC-FID (200 μL of reaction mixture was collected, quenched with 4 μL of ethyl vinyl ether and analysed at this concentration).

Example 25

CM of 15 and 16 at 0.02 M Concentration in PFR-V

A reaction was carried out and monitored as described for PFR with the use of PFR-V in which internal tube was connected with the high vacuum pump (pressure was in the range of 0.05-0.07 mbar).

The results of CM are collected in Table 7 and Table 8.

TABLE 7

CM of methyl undecenoate with methyl acrylate at 0.2M concentration

| Entry | Flow rate [mL/h] | Reaction time [min] | Conversion [%][a] BR | PFR-V | PFR |
|---|---|---|---|---|---|
| 1 | 48 | 2.5 | 86 | 79 | 79 |
| 2 | 24 | 5 | 91 | 82 | 89 |
| 3 | 12 | 10 | 92 | 86 | 88 |
| 4 | 8 | 15 | 93 | 89 | 88 |
| 5 | 6 | 20 | 94 | 91 | 87 |
| 6 | 4 | 30 | 95 | 93 | 86 |

[a]final E/Z ratio 94/6 in all cases

TABLE 8

CM of methyl undecenoate with methyl acrylate at 0.02M concentration

| Entry | Flow rate [mL/h] | Reaction time [min] | Conversion [%][a] BR | PFR-V | PFR |
|---|---|---|---|---|---|
| 1 | 24 | 5 | 80 | 77 | 60 |
| 2 | 12 | 10 | 85 | 81 | 62 |
| 3 | 8 | 15 | 87 | 87 | 57 |
| 4 | 6 | 20 | 89 | 89 | 60 |
| 5 | 4 | 30 | 91 | 92 | 61 |

[a]final E/Z ratio 93/7 in all cases

As illustrated in Examples 2-25 PFR-V can give superior results in olefin metathesis reactions when compared with simple PFR. Moreover, for some transformations PFR-V gives better results than BR.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

Even further, "specific embodiments disclosed herein may be further limited in the claims using consisting of or and consisting essentially of language. When used in the claims, whether as filed or added per amendment, the transition term "consisting of" excludes any element, step, or ingredient not specified In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A reactor for olefin metathesis reactions in a continuous flow mode comprising:
   an impermeable outer tube and an inner semi-permeable tube;
   wherein a reaction zone is defined between an inner surface of the impermeable outer tube and an outer surface of the inner semi-permeable tube, and wherein contents of the inner semi-permeable tube are pumped away using a vacuum source.

2. The reactor of claim 1, wherein the semi-permeable tube is permeable to one or more by-products of olefin metathesis reactions.

3. The reactor of claim 2, wherein the one or more by-products is ethylene.

4. The reactor of claim 2, wherein the one or more by-products is acetylene.

5. The reactor of claim 1, wherein the semi-permeable tube is permeable to one or more by-products having 2 or 3 carbon atoms.

6. The reactor of claim 5, wherein the semi-permeable tube is not permeable to one or more products having more than 6 carbon atoms.

7. The reactor of claim 1, wherein the semi-permeable tube is permeable to one or more by-products having a boiling point below about 60° C.

8. The reactor of claim 7, wherein the semi-permeable tube is not permeable to one or more products having a boiling point above about 60° C.

9. The reactor of claim 1 configured to accept at least one substrate and optionally at least one catalyst at a proximal end of the reactor.

10. The reactor of claim 1 configured to expel at least one product at port at a distal end of the reactor.

11. The reactor of claim 1, further comprising a heterogeneous catalyst housed in the reaction zone.

12. A reactor for olefin metathesis reactions in a continuous flow mode comprising:
    an impermeable outer tube and an inner semi-permeable tube;
    wherein a reaction zone is defined within the semi-permeable tube, and wherein the contents of a space defined between inner surface of the impermeable outer tube and an outer surface of the inner semi-permeable tube are pumped away using a vacuum source.

13. The reactor of claim 7, wherein the semi-permeable tube is permeable to one or more by-products of olefin metathesis reactions.

14. The reactor of claim 13, wherein the one or more by-products is ethylene.

15. The reactor of claim 13, wherein the one or more by-products is acetylene.

16. The reactor of claim 12, wherein the semi-permeable tube is permeable to one or more by-products having 2 or 3 carbon atoms.

17. The reactor of claim 16, wherein the semi-permeable tube is not permeable to one or more products having more than 6 carbon atoms.

18. The reactor of claim 12, wherein the semi-permeable tube is permeable to one or more by-products having a boiling point below about 60° C.

19. The reactor of claim 18, wherein the semi-permeable tube is not permeable to one or more products having a boiling point above about 60° C.

20. The reactor of claim 12 configured to accept at least one substrate and optionally at least one catalyst at a proximal end of the reactor.

21. The reactor of claim 12 configured to expel at least one product at port at a distal end of the reactor.

22. The reactor of claim 12, further comprising a heterogeneous catalyst housed in the reaction zone.

23. A method of performing olefin metathesis reactions in a continuous flow mode comprising:
reacting at least one substrate and at least one catalyst in a reaction zone of a tube-in-tube reactor, wherein the tube-in-tube reactor includes an impermeable outer tube and an inner semi-permeable tube;
wherein the reaction zone is defined between an inner surface of the impermeable outer tube and an outer surface of the inner semi-permeable tube, and wherein the contents of the inner semi-permeable tube are pumped away using a vacuum source.

24. A method of performing olefin metathesis reactions in a continuous flow mode comprising:
reacting at least one substrate and at least one catalyst in a reaction zone of a tube-in-tube reactor, wherein the tube-in-tube reactor includes an impermeable outer tube and an inner semi-permeable tube;
wherein a reaction zone is defined within the semi-permeable tube, and wherein the contents of a space defined between inner surface of the impermeable outer tube and an outer surface of the inner semi-permeable tube are pumped away using a vacuum source.

\* \* \* \* \*